(12) United States Patent
Levenson et al.

(10) Patent No.: US 9,588,099 B2
(45) Date of Patent: *Mar. 7, 2017

(54) SPECTRAL IMAGING

(71) Applicant: Cambridge Research & Instrumentation, Inc., Hopkinton, MA (US)

(72) Inventors: Richard Levenson, Brighton, MA (US); Paul J. Cronin, Allen, TX (US)

(73) Assignee: Cambridge Research & Intrumentation, Inc., Hopkinton, MA (US)

( * ) Notice: Subject to any disclaimer, the term of this patent is extended or adjusted under 35 U.S.C. 154(b) by 195 days.

This patent is subject to a terminal disclaimer.

(21) Appl. No.: 13/760,193

(22) Filed: Feb. 6, 2013

(65) Prior Publication Data

US 2013/0300848 A1 Nov. 14, 2013

Related U.S. Application Data

(63) Continuation of application No. 11/522,745, filed on Sep. 18, 2006, now Pat. No. 8,391,961, which is a (Continued)

(51) Int. Cl.
*G01N 21/64* (2006.01)
*A61B 5/00* (2006.01)
(Continued)

(52) U.S. Cl.
CPC ....... *G01N 33/4833* (2013.01); *A61B 5/0059* (2013.01); *B82Y 5/00* (2013.01);
(Continued)

(58) Field of Classification Search
None
See application file for complete search history.

(56) References Cited

U.S. PATENT DOCUMENTS

| 4,379,233 A | 4/1983 | Rosenthal |
| 4,519,707 A | 5/1985 | Kuffer |
| (Continued) | | |

FOREIGN PATENT DOCUMENTS

| EP | 512965 | 11/1992 |
| WO | WO 98/43042 | 10/1998 |
| (Continued) | | |

OTHER PUBLICATIONS

Richard M. Levenson et al., "Multispectral imaging for multicolor immunohistochemical and transmission in-situ hybridization," *Acta Histochem. Cytochem.* 35(3): 225 (2002).
(Continued)

*Primary Examiner* — Long V Le
*Assistant Examiner* — Bradley Impink
(74) *Attorney, Agent, or Firm* — Fish & Richardson P.C.

(57) ABSTRACT

Apparatus and methods are provided for the imaging of structures in deep tissue within biological specimens, using spectral imaging to provide highly sensitive detection. By acquiring data that provides a plurality of images of the sample with different spectral weightings, and subsequent spectral analysis, light emission from a target compound is separated from autofluorescence in the sample. With the autofluorescence reduced or eliminated, an improved measurement of the target compound is obtained.

28 Claims, 10 Drawing Sheets

Related U.S. Application Data continuation of application No. 10/669,101, filed on Sep. 23, 2003, now Pat. No. 7,321,791.

(51) Int. Cl.
| | |
|---|---|
| *G01N 33/483* | (2006.01) |
| *B82Y 5/00* | (2011.01) |
| *B82Y 10/00* | (2011.01) |
| *G01J 3/32* | (2006.01) |
| *G01J 3/44* | (2006.01) |
| *G01J 3/453* | (2006.01) |
| *G01N 21/25* | (2006.01) |

(52) U.S. Cl.
CPC ............ *B82Y 10/00* (2013.01); *G01J 3/32* (2013.01); *G01J 3/4406* (2013.01); *G01J 3/453* (2013.01); *G01N 21/255* (2013.01); *G01N 21/6486* (2013.01); *G01N 2201/062* (2013.01); *G01N 2201/125* (2013.01)

(56) References Cited

U.S. PATENT DOCUMENTS

| | | | |
|---|---|---|---|
| 4,669,878 A | 6/1987 | Meier | |
| 4,800,279 A | 1/1989 | Hieftji et al. | |
| 5,029,245 A | 7/1991 | Keranen et al. | |
| 5,042,893 A | 8/1991 | Ong | |
| 5,066,124 A | 11/1991 | Wulf | |
| 5,115,137 A | 5/1992 | Andersson-Engels et al. | |
| 5,137,364 A | 8/1992 | McCarthy | |
| 5,424,545 A | 6/1995 | Block et al. | |
| 5,433,197 A | 7/1995 | Stark | |
| 5,507,287 A | 4/1996 | Palcic et al. | |
| 5,539,517 A | 7/1996 | Cabib et al. | |
| 5,567,937 A | 10/1996 | Pinkus | |
| 5,608,213 A | 3/1997 | Pinkus et al. | |
| 5,647,368 A | 7/1997 | Zeng et al. | |
| 5,719,024 A | 2/1998 | Cabib et al. | |
| 5,749,830 A * | 5/1998 | Kaneko et al. | 600/160 |
| 5,760,407 A | 6/1998 | Margosiak et al. | |
| 5,827,190 A | 10/1998 | Palcic et al. | |
| 5,834,203 A | 11/1998 | Katzir et al. | |
| 5,838,451 A | 11/1998 | McCarthy | |
| 5,912,165 A | 6/1999 | Cabib et al. | |
| 5,941,818 A * | 8/1999 | Hori et al. | 600/143 |
| 5,991,028 A | 11/1999 | Cabib et al. | |
| 5,995,645 A | 11/1999 | Soenksen et al. | |
| 5,999,844 A | 12/1999 | Gombrich et al. | |
| 6,002,137 A | 12/1999 | Hayashi | |
| 6,007,996 A | 12/1999 | McNamara et al. | |
| 6,051,835 A | 4/2000 | Pettipiece et al. | |
| 6,075,595 A | 6/2000 | Malinen | |
| 6,142,629 A | 11/2000 | Adel et al. | |
| 6,160,617 A | 12/2000 | Yang | |
| 6,160,618 A | 12/2000 | Garner | |
| 6,232,523 B1 | 5/2001 | Tan et al. | |
| 6,235,968 B1 | 5/2001 | Tan et al. | |
| 6,236,881 B1 | 5/2001 | Zahler et al. | |
| 6,251,384 B1 | 6/2001 | Tan et al. | |
| 6,272,376 B1 | 8/2001 | Marcu et al. | |
| 6,289,229 B1 | 9/2001 | Crowley | |
| 6,300,639 B1 | 10/2001 | Wiederhoeft | |
| 6,364,829 B1 | 4/2002 | Fulghum | |
| 6,373,568 B1 | 4/2002 | Miller et al. | |
| 6,393,315 B1 | 5/2002 | Aprahamian et al. | |
| 6,421,131 B1 | 7/2002 | Miller | |
| 6,466,687 B1 | 10/2002 | Uppaluri et al. | |
| 6,556,853 B1 | 4/2003 | Cabib et al. | |
| 6,649,159 B2 | 11/2003 | Yang et al. | |
| 6,665,438 B1 | 12/2003 | Lin | |
| 6,690,466 B2 | 2/2004 | Miller et al. | |
| 6,690,817 B1 | 2/2004 | Cabib et al. | |
| 6,750,964 B2 * | 6/2004 | Levenson et al. | 356/326 |
| 6,759,038 B2 | 7/2004 | Tan et al. | |
| 6,776,760 B2 | 8/2004 | Marmarelis | |
| 6,821,245 B2 | 11/2004 | Cline et al. | |
| 6,891,613 B2 | 5/2005 | Wolleschensky et al. | |
| 6,920,239 B2 | 7/2005 | Douglass et al. | |
| 6,924,893 B2 | 8/2005 | Oldenbourg et al. | |
| 6,930,773 B2 * | 8/2005 | Cronin et al. | 356/300 |
| 6,952,499 B1 | 10/2005 | Vititoe | |
| 6,954,667 B2 | 10/2005 | Treado et al. | |
| 7,009,699 B2 | 3/2006 | Wolleschensky et al. | |
| 7,151,270 B2 | 12/2006 | Birk et al. | |
| 7,321,791 B2 | 1/2008 | Levenson et al. | |
| 7,519,206 B2 | 4/2009 | Mulet-Parada et al. | |
| 7,640,140 B2 | 12/2009 | Ruchti et al. | |
| 7,679,740 B2 | 3/2010 | Neiss et al. | |
| 7,689,023 B2 | 3/2010 | Rabinovich | |
| RE41,333 E | 5/2010 | Blank et al. | |
| 7,873,407 B2 * | 1/2011 | Levenson et al. | 600/476 |
| 7,920,736 B2 | 4/2011 | Sammak et al. | |
| 7,945,077 B2 | 5/2011 | Demos | |
| 7,990,532 B2 | 8/2011 | Neiss et al. | |
| 8,019,134 B2 | 9/2011 | Athelogou et al. | |
| 8,103,081 B2 | 1/2012 | Gossage et al. | |
| 8,116,548 B2 | 2/2012 | Zheng et al. | |
| 8,154,612 B2 | 4/2012 | Quan et al. | |
| 8,385,615 B2 * | 2/2013 | Levenson et al. | 382/128 |
| 8,391,961 B2 * | 3/2013 | Levenson et al. | 600/476 |
| 8,634,607 B2 * | 1/2014 | Levenson et al. | 382/128 |
| 2002/0022766 A1 | 2/2002 | Adachi | |
| 2002/0035330 A1 | 3/2002 | Cline et al. | |
| 2003/0081204 A1 | 5/2003 | Cronin et al. | |
| 2003/0123056 A1 | 7/2003 | Barnes et al. | |
| 2003/0135092 A1 | 7/2003 | Cline et al. | |
| 2003/0138140 A1 | 7/2003 | Marcelpoil et al. | |
| 2003/0179372 A1 | 9/2003 | Knebel | |
| 2003/0223248 A1 | 12/2003 | Cronin et al. | |
| 2004/0006275 A1 | 1/2004 | Demos et al. | |
| 2004/0006276 A1 | 1/2004 | Demos et al. | |
| 2004/0081621 A1 | 4/2004 | Arndt et al. | |
| 2004/0181375 A1 | 9/2004 | Szu et al. | |
| 2004/0225222 A1 | 11/2004 | Zeng et al. | |
| 2005/0065406 A1 | 3/2005 | Cline et al. | |
| 2005/0065440 A1 * | 3/2005 | Levenson | 600/476 |
| 2005/0143627 A1 | 6/2005 | Cline et al. | |
| 2005/0171434 A1 | 8/2005 | Madden et al. | |
| 2005/0243313 A1 | 11/2005 | Neher et al. | |
| 2006/0074282 A1 | 4/2006 | Ward et al. | |
| 2006/0129040 A1 | 6/2006 | Fine et al. | |
| 2006/0220881 A1 | 10/2006 | Al-Ali et al. | |
| 2006/0241496 A1 | 10/2006 | Fengler et al. | |
| 2007/0015963 A1 | 1/2007 | Fengler et al. | |
| 2007/0016078 A1 * | 1/2007 | Hoyt et al. | 600/476 |
| 2007/0016082 A1 | 1/2007 | Levenson et al. | |
| 2007/0080305 A1 | 4/2007 | Maitrejean et al. | |
| 2007/0135999 A1 | 6/2007 | Kolatt | |
| 2007/0249913 A1 | 10/2007 | Freeman et al. | |
| 2008/0051665 A1 | 2/2008 | Xu et al. | |
| 2008/0294032 A1 | 11/2008 | Levenson et al. | |
| 2009/0048785 A1 | 2/2009 | Katzir et al. | |
| 2009/0245605 A1 | 10/2009 | Levenson et al. | |
| 2010/0034453 A1 | 2/2010 | Lynch | |
| 2011/0238325 A1 | 9/2011 | Lett et al. | |
| 2014/0134713 A1 * | 5/2014 | Levenson et al. | 435/288.7 |

FOREIGN PATENT DOCUMENTS

| | | |
|---|---|---|
| WO | WO 98/46133 | 10/1998 |
| WO | WO 99/18847 | 4/1999 |
| WO | WO 01/11343 | 2/2001 |
| WO | WO 2005/040769 | 5/2005 |
| WO | WO 2009/006696 | 1/2009 |

OTHER PUBLICATIONS

Richard Levenson et al., "Whole-body spectral imaging of fluorescently labeled orthotopic lung tumors in the live mouse," *Proceedings of the American Association for Cancer Research*, vol. 44, 2nd ed., p. 675 (Jul. 2003).

(56) References Cited

OTHER PUBLICATIONS

Richard Levenson et al., "Whole-body spectral imaging of fluorescently labeled orthotopic tumors in the live mouse," Poster 3394, AACR 2003 Conference.
Selim Aksoy et al., "Textural Features for Image Database Retrieval", IEEE, pp. 45-49 (1998).
Amoh, Y. et al., "Hair follicle-derived blood vessels vascularize tumors in skin and are inhibited by doxorubicin", Cancer Res. vol. 65, pp. 2337-2343 (2005).
Amoh, Y. et al., Nestin-linked green fluorescent protein transgenic nude mouse for imaging human tumor angiogenesis. Cancer Res. 65, 5352-5357, 2005.
Amoh, Y. et al., "Dual-color imaging of nascent blood vessels vascularizing pancreatic cancer in an orthotopic model demonstrates antiangiogenesis efficacy of gemcitabine", J. Surgical Research, vol. 132, pp. 164-169 (2006).
Amoh, Y. et al., "Dual-color imaging of nascent angiogenesis and its inhibition in liver metastases of pancreatic cancer", Anticancer Research, vol. 26, pp. 3237-3242 (2006).
P.S. Andersson et al. "Flourescence Endoscopy Instrumentation for Improved Tissue Characterization." Med. Phys. 14 (4) Jul./Aug. 1987. 633-636.
Jeremy J. Andrew, et al., "Rapid Analysis of Raman Image Data Using Two-Way Multivariate Curve Resolution", Applied Spectroscopy, vol. 52, No. 6, pp. 797-807 (1998).
Nicholas Billinton et al., "Seeing the Wood through the Trees: A Review of Techniques for Distinguishing Green Fluorescent Protein from Endogenous Autofluorescence", Analytical Biochemistry, vol. 291, pp. 175-197 (2001).
Bishop, Christopher M., "The Multi-Layer Perceptron", Neural Networks for Pattern Recognition (Oxford University Press, 1995), pp. 116-163.
K.J. Brodbeck et al. "A System for Real Time Flourescence Imaging in Color for Tumor Diagnosis." Med. Phys. 14 (4) Jul./Aug. 1987 637-639.
Kenneth P. Camilleri et al., "Spectral Unmixing of Mixed Pixels for Texture Boundary Refinement", IEEE, pp. 1084-1087 (2000).
Kenneth R. Castleman, "Color compensation for digitized FISH images", Bioimaging 1, pp. 159-165 (1993).
R. Cubeddu et al., "Time-gated Fluorescence Spectroscopy and Imaging of Porphyrins and Phthalocyanines", SPIE, vol. 1525, pp. 17-25 (1991).
Mary E. Dickinson et al., "Multiphoton excitation spectra in biological samples", Journal of Biomedical Optics, vol. 8, No. 3, pp. 329-338 (Jul. 2003).
Richard O. Duda, et al., "Chapter 10—Unsupervised Learning and Clustering", Pattern Classification, pp. 517-599, John Wiley & Sons, Inc., New York, NY (2001).
Silvio Folli et al., "Antibody-Indocyanin Conjugates for Immunophotodetection of Human Squamous Cell Carcinoma in Nude Mice", Cancer Research, vol. 54, pp. 2643-2649 (May 15, 1994).
S. Folli at al. "Immunophotodiagnosis of Colon Carcinomas in Patients Injected with Flouresceinated Chimerica Antibodies Against Carcinoembryionic Antigen." Institute of Biochemistry, University of Lausanne, Switzerland. 7973-7977. (Sep. 1992).
Gentry et al., Biomedical Applications of the Inforination-Efficient Spectral Imaging Sensor (ISIS), Gentry, SPIE vol. 3603, pp. 129-142. (Jan. 1999).
David Gillis et al. "Using Endmembers as a Coordinate System in Hyperspectral Imagery," Naval Research Laboratory, Washington, DC. 1-9. (2002).
Andrew A. Green et al. "A Transformation for Ordering Multispectral Data in Terms of Image Quality with Implications for Noise Removal." IEEE Transactions of Geoscience and Remote Sensing vol. 26, No. 1 Jan. 1988. 65-74.
Haralick, R.M. et al., "Textural features for image classification", IEEE Transactions on Systems, Man, and Cybernetics, vol. SMC-3: 610-621 (1973).

Jacqueline Hewett et al., "The Application of a Compact Multispectral Imaging System with Integrated Excitation Source to In vivo Monitoring of Fluorescence During Topical Photodynamic Therapy of superficial Skin Cancers", Photochemistry and Photobiology, vol. 73, No. 3, pp. 275-282 (2001).
Klaus B. Hilger et al. "MADCAM—The Multispectral Active Decomposition Camera." IMM, Informatics and Mathematical Modelling, Technical University of Denmark, 1-7. (2001).
Yasushi Hiraoka et al., "Multispectral Imaging Fluorescence Miscroscopy for Living Cells", Cell Structure and Function, No. 27, pp. 367-374 (2002) by Japan Society for Cell Biology.
Hyvarien et al., "Novel Spectroscopic Techniques for Biomedical Applications," Optoelectronics Laboratory, Finland, SPIE vol. 2084, pp. 224-230. (Aug. 1994).
L.O. Jimenez et al., "High Dimensional Feature Reduction via Projection Pursuit," TR-ECE 96-5, School of Electrical Engineering, Purdue University, West Lafayette, IN 47907-1285, Apr. 1995.
Jimenez, L. et al., "Hyperspectral Data Analysis and Feature Reduction Via Projection in Pursuit", IEEE Transactions on Geoscience and Remote Sensing 37(6): 2653-2667 (1999).
Luis Jimenez et al., "Supervised Classification in High Dimensional Space: Geometrical, Statistical and Asymptotical Properties of Multivariate Data", IEEE Transactions on Geoscience and Remote Sensing, vol. 37, No. 6, pp. 1-32 (Nov. 1999).
Keraanen et al., "Thirty-two Channel LED Array Spectrometer Module with Compact Optomechanical Construction," Technical Research Centre of Finland, Electronics Laboratory, Finland, SPIE, vol. 1533 Optomechanics and Dimensional Stability (1991), pp. 122-128.
Nirmal Keshava et al. "Spectral Unmixing." IEEE Signal Processing Magazine. Jan. 2002. 44-57.
M. Kohl et al., "Imaging of tumors by time-delayed laser-induced fluorescence", SPIE, vol. 1525, pp. 26-34 (1991).
David Landgrebe. "Hyperspectral Image Data Analysis." IEEE Signal Processing Magazine, Jan. 2002. 17-28.
David Landgrebe. "Information Extraction Principles and Methods for Mutispectral and Hyperspectral Image Data." School of Electrical and Computer Engineering. (1998) 1-29.
Dimitris Manolakis et al. "Detection Algorithms for Hyperspectral Imaging Applications." IEE Signal Processing Magazine. Jan. 2002. 29-43.
Paul M. Mather, "Classification 'What is or is not a cow is for the public to decide'", Computer Processing of Remotely-Sensed Images: An Introduction, Third Edition, John Wiley & Sons, Ltd. (2004).
Jose M.P. Nascimento. "Vertex Component Analysis: A Fast Algorithm to Unmix Hyperspectral Data." 1-23. (2005).
R.A Neville et al. "Automatic Endmember Extraction from Hyperspectral Data for Mineral Exploration." Fourth International Airborne Remote Sensing Conference and Exhibition Jun. 1999. 1-8.
Andre Pelegrin et al., "Antibody-Fluorescein Conjugates for Photoimmunodiagnosis of Human Colon Carcinoma in Nude Mice", Cancer, vol. 67, pp. 2529-2537 (May 15, 1991).
Antonio Plaza et al. "A Quantitative and Comparitive Analysis of Endmember Extraction Algorithms from Hyperspectral Data." IEEE Transactions on Geoscience and Remote Sensing vol. 42 No. 3, Mar. 2004. 650-663.
Antonio Plaza et al. "Spatial/Spectral Endmember Extraction by Multidimensional Mophoiogical Operations." IEEE Transactions on Geoscience and Remote Sensing vol. 40, No. 9 Sep. 2002. 2025-2041.
F.P. Seelos IV et al. "Bounded Variable Least Squares—Application of a Constrained Optimization Algorithm to the Analysis of TES Emmisivity Spectra." Lunar and Planetary Sciences XXXIV (2003) 56-69.
Shnitser et al., "Spectrally Adaptive Light Filtering," Physical Optics Corporation, Torrance, CA, SPIE vol. 3140, pp. 117-127. (1997).
B.R. Stallard, Construction of Filter Vectors for the Information-Efficient Spectral Imaging Sensor, Imaging Spectroscopy IV, Proc. SPIE, vol. 3438, pp. 172-182, San Diego, 1998.

(56) References Cited

OTHER PUBLICATIONS

David W. J. Stein et al. "Anomaly Detection from Hyperspectral Imagery." IEEE Signal Processing Magazine. Jan. 2002. 58-69.
Karatina Svanberg et al., "Fluorescence Studies of Hematoporphyrin Derivative in Normal and Malignant Rat Tissue", *Cancer Research*, vol. 46, pp. 3803-3808 (Aug. 1986).
W.C. Sweatt et al., "ISIS; An Information-Efficient Spectral Imaging System," Imaging Spectrometry IV, Proc. SPIE, vol. 3438, pp. 98-106, San Diego, 1998.
Tamara Troy et. al. "Quantitative Comparison of the Sensitivity of Detection of Flourescent and Bioluminescent Reporters in Animal Models." Molecular Imaging vol. 5 No. 1, Jan. 2004. 9-23.
Eric Van Leengoed at al., "Tissue-Localizing Properties of Some Photosensitizers Studied by in vivo Fluorescence Imaging", *Journal of Photochemistry and Photobiology, B: Biology*, vol. 6, pp. 111-119 (1990).
G. Wagnieres et al., "Photodetection of Early Cancer in the Upper Aerodigestive Tract and the Bronchi using Photofrin II and Colorectal Adenocarcinoma with Fluoresceinated Monoclonal Antibodies", *SPIE*, vol. 1525, pp. 219-236 (1991).
Stephen W. Wharton, "A Contextual Classification Method for Recognizing Land Use Patterns in High Resolution Remotely Sensed Data", Pattern Recognition, vol. 15, No. 4, pp. 317-324 (1982).
Stefan Wild et al. "Motivating Non-Negative Matrix Factorizations." Department of Applied Mathematics, University of Colorado, 1-11. (2003).
Michael E. Winter. "Fast Autonomous Spectral Endmember Determination in Hyperspectral Data." 13$^{th}$ Internation Conference on Applied Geologic Remote Sensing, Mar. 1-3, 1999. 1-16.
Michael E. Winter. "N-FTNDR: An Algorithm for Fast Autonomous Spectral End-Member Determination in Hyperspectral Data." Department of Earth Sciences. 1-8. (1999).
Yang, M. Et al., "Whole-body and intravital optical imaging of angiogenesis in orthotopically implanted tumors", *Proc. Natl. Acad. Sci. USA*, vol. 98, pp. 2616-2621 (2001).
Yang, M. et al., "Direct external imaging of nascent cancer, tumor progression, angiogenesis, and metastasis on internal organs in the fluorescent orthotopic model", *Proc. Natl. Acad. Sci. USA*, vol. 99, pp. 3824-3829 (2002).
Yang, M. et al., "Dual-color fluorescence imaging distinguishes tumor cells from induced host angiogenic vessels and stromal cells", *Proc. Natl. Acad. Sci. USA*, vol. 100, pp. 14259-14262 (2003).
Yang, M. et al., "Transgenic nude mouse with ubiquitous green fluorescent protein expression as a host for human tumors", *Cancer Research*, vol. 64, pp. 8651-8656 (2004).
Yang, M. et al., "Whole-body subcellular multicolor imaging of tumor-host interaction and drug response in real time", *Cancer Res.*, vol. 67, pp. 5195-5200 (2007).
Yang, M. at al., "Facile whole-body imaging of internal fluorescent tumors in mice with an LED flashlight", *BioTechniques*, vol. 39, pp. 170-172 (2005).
European Search Report for Application No. 06014263.5-2305 dated Oct. 10, 2007.

\* cited by examiner

SPECTRAL IMAGING

CROSS REFERENCE TO RELATED APPLICATION

Pursuant to U.S.C. §120, this application is a continuation of prior U.S. application Ser. No. 11/522,745, filed on Sep. 18, 2006, entitled "SPECTRAL IMAGING", which is a continuation of prior U.S. application Ser. No. 10/669,101, filed on Sep. 23, 2003, now U.S. Pat. No. 7,321,791, entitled "SPECTRAL IMAGING OF DEEP TISSUE." The contents of the prior applications are incorporated herein by reference in their entirety.

BACKGROUND

Optical imaging of deep tissue is used to probe structures within biological specimens for laboratory research and biomedical purposes. This includes the imaging of internal organs and subdermal tissue in animals such as mice, zebrafish, or humans, and one of the goals is to learn about internal structures without surgery or other intrusive measures.

In one technique of deep tissue imaging, fluorescent probes which bind to a specific target in the specimen are imaged by exciting them with illumination light, causing them to fluoresce; the fluorescent emission is separated from the illumination light, which has a different wavelength, by barrier filters and then is detected using a very sensitive camera such as a cooled CCD detector. In other techniques, the specimen is infected with agents that cause it to produce material that is inherently fluorescent, with the most common example being green fluorescent protein (GFP). Further techniques involve use of quantum dots as luminous probes.

As used herein, compounds such as fluorescent probes, GFP, or quantum dots, as well as related compounds or others used for similar purposes, are all termed the target compounds of a measurement.

The signals produced in such experiments are typically weak. In general, robust detection of the weak levels of light emitted from the deep structures is beneficial because it provides earlier, or more reliable, detection of the structures being studied. Also, it may enable detection of lower levels of the target compound. Accordingly, techniques or apparatus used for deep tissue imaging are valued if they offer a low detection threshold.

SUMMARY

The present invention features a method and apparatus to improve detection of target compounds such as GFP, quantum dots, and fluorescent probes used for deep tissue imaging in a variety of biological samples. Moreover, the method and apparatus are generally compatible with use of such compounds, without requiring extreme sensitivity from the imaging detector.

The method and apparatus use spectral imaging to distinguish between undesired autofluorescence signals arising from various sites in the specimen, and the desired signal from the target compound. It has been discovered that the spectral information thus obtained provides improved detection sensitivity and can be used for deep tissue imaging, even though there is typically significant optical loss in the spectral selection elements of the system.

In one embodiment, images are taken while viewing the emission light from the specimen at a sequence of wavelengths, to develop an image cube with two spatial dimensions and a spectrum at each point. By determining the difference in spectral properties between the desired target compound emission and the unwanted autofluorescence emission, the overall signal is decomposed into components and the detection levels for the desired compound emission are greatly improved.

Other embodiments include measurements based on brightness ratios at several selected wavelengths or wavelength bands; measurements based on principal component analysis; and measurements based on neural networks, and on fuzzy logic.

In either case, the method and apparatus use spectral information to distinguish the desired signal emitted by the target compound from the unwanted autofluorescence signal, and thus to improve the measurement integrity and sensitivity.

Various aspects and features of the invention will now be summarized.

In general, in one aspect, the invention features a method including: (i) illuminating a sample to cause the sample to emit radiation, wherein the sample includes deep tissue supporting a target compound, and wherein the emitted radiation includes emission from the target compound and emission from one or more other components in the sample; (ii) spectrally filtering the emitted radiation with each of a plurality of different spectral weighting functions; (iii) storing an image of the spectrally filtered radiation for each of the spectral weighting functions; and (iv) processing the stored images to construct a deep tissue image of the sample in which signal from the other compounds is reduced relative to signal from the target compound.

In general, in another aspect, the invention features a method including: (i) providing a plurality of images of spectrally filtered radiation emitted from a sample in response to an illumination, wherein the sample includes deep tissue supporting a target compound, wherein the emitted radiation includes emission from the target compound and emission from one or more other components in the sample, and wherein each image corresponds to a different spectral weighting function; and (ii) processing the images of the spectrally filtered radiation to construct a deep tissue image of the sample in which signal from the other compounds is reduced relative to signal from the target compound.

In general, in yet another aspect, the invention features an apparatus including a computer readable medium which stores a program that causes a processor to: (i) receive a plurality of images of spectrally filtered radiation emitted from a sample in response to an illumination, wherein the sample includes deep tissue supporting a target compound, wherein the emitted radiation includes emission from the target compound and emission from one or more other components in the sample, and wherein each image corresponds to a different spectral weighting function; and (ii) process the images of the spectrally filtered radiation to construct a deep tissue image of the sample in which signal from the other compounds is reduced relative to signal from the target compound.

In general, in yet another aspect, the invention features an apparatus comprising: (i) a sample holder configured to hold a sample including deep tissue, wherein the deep tissue supports a target compound; (ii) an illumination source configured to illuminate the sample to cause it to emit radiation, wherein the emitted radiation includes emission from the target compound and emission from one or more other components in the sample; (iii) an imaging system configured to image the emitted radiation to a detector; (iv)

a tunable spectral filter configured to spectrally filter the emitted radiation with each of a plurality of different spectral weighting functions; (v) a detector configured to store an image of the spectrally filtered radiation for each of the spectral weighting functions; and (vi) a electronic processor configured to process the store images to construct a deep tissue image of the sample in which signal from the other compounds is reduced relative to signal from the target compound. For example, the sample holder may configured to hold an animal, such as a mammal, like a mouse, rabbit, or human. Also, for example, the imaging system may have a demagnification greater than or equal to 1, and, for example, the imaging system may be configured to image a field of view having a diagonal dimension greater than about 2 cm onto the detector.

Embodiments of the various aspects of the invention described above may include any of the following features.

The sample including the deep tissue may be a living organism, such as an animal or a mammal. For example, the animal may include a mouse, a rabbit, a zebrafish, or a human. Also, the deep tissue may be an internal organ of the living organism, and the deep tissue may lie within about 2 mm or more of the living organism.

The deep tissue may be subdermal tissue.

The emission from the other components of the sample may include autofluorescence from tissue overlying the deep tissue.

The emission from the other components of the sample may include autofluorescence from one or more layers of tissue in the sample different from a layer of tissue including the deep tissue.

The target compound may be any of, for example, a fluorescent probe bound to at least a portion of the deep tissue, a quantum dot bound to at least a portion of the deep tissue, a green fluorescent protein (GFP) bound to at least a portion of the deep tissue, a yellow fluorescent protein (YFP) bound to at least a portion of the deep tissue, and a red fluorescent protein (RFP) bound to at least a portion of the deep tissue.

The emission from the target compound may be fluorescence.

At least some of the spectral weighting functions may correspond to particular wavelength bands. For example, all of the spectral weighting functions correspond to particular wavelength bands. Alternatively, at least some of the spectral weighting functions may correspond to sinusoidal weightings of multiple wavelength bands.

The spectral filtering may include using any of a liquid-crystal, tunable optical filter, an interferometric optical filter, and a filter wheel containing a plurality of band pass filters.

Each stored image may include an intensity value for each of multiple pixels.

Processing the stored images may include constructing the deep tissue image based on a weighted superposition of signals in the stored images.

Processing the recorded images may include constructing the deep tissue image based on the recorded images and at least one emission spectrum for the other components in the sample. For example, constructing the deep tissue image may include calculating a remainder spectrum for each pixel in the set of stored images based on the at least one emission spectrum for the other components.

Similarly, processing the recorded images may include constructing the deep tissue image based on the recorded images and an emission spectrum for the target compound. For example, constructing the deep tissue image may include calculating a remainder spectrum for each pixel in the set of stored images based on the emission spectrum for the target compound.

Also, processing the recorded images may include constructing the deep tissue image based on the recorded images, at least one emission spectrum for the other components in the sample, and an emission spectrum for the target compound. For example, constructing the deep tissue image may include solving at least one component of a matrix equation in which one matrix is based on the stored images, and another matrix is based on the emission spectra.

The deep tissue may support multiple target compounds and processing the stored images may include constructing a deep tissue image for each of the target compounds. For example, processing the recorded images may include constructing the deep tissue images based on the recorded images and emission spectra for the target compounds. Furthermore, processing the recorded images may include constructing the deep tissue images based on the recorded images, the emission spectra for the target compounds, and at least one emission spectrum for the other components in the sample.

The plurality of the different spectral weighting functions may include four or more spectral weighting functions.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control.

Other features, objects, and advantages of the invention will be apparent from the following detailed description.

DESCRIPTION OF DRAWINGS

The invention will now be further described merely by way of example with reference to the accompanying drawings.

Like reference symbols in the various drawings indicate like elements.

DETAILED DESCRIPTION

The invention features a method and apparatus for reducing the detection level of a target compound in deep tissue through spectral discrimination. An important aspect is that a beneficial result is obtained despite the low light levels involved.

Figure 10:
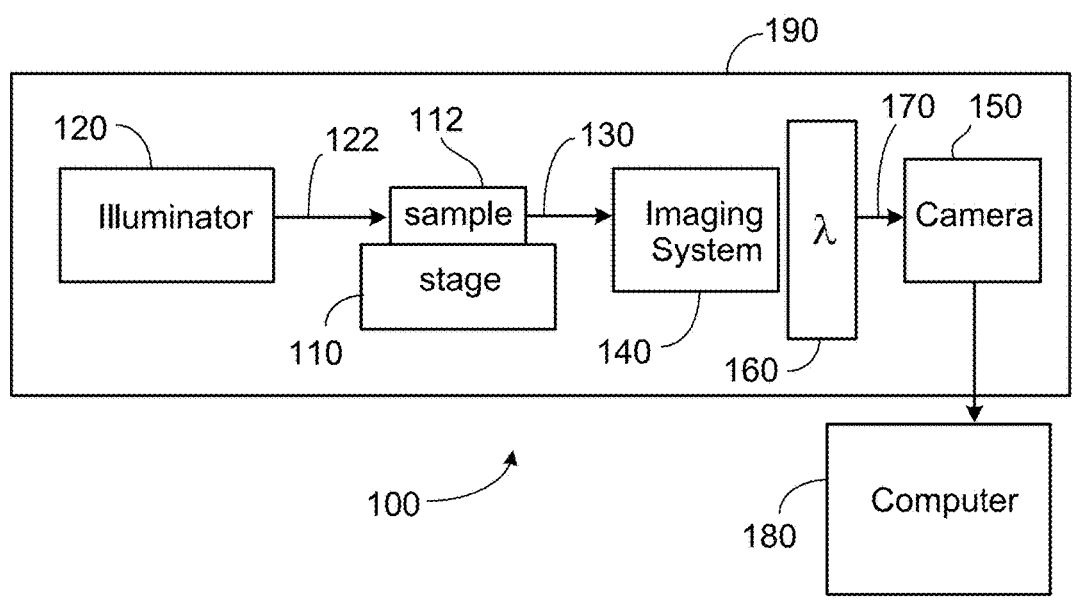
FIG. 10 is a schematic diagram of a spectral imaging system.

A schematic diagram of a spectral imaging system 100 for imaging deep tissue is shown in FIG. 10. System 100 includes a sample holder 110 suitable for holding a specimen 112 having deep tissue. For example, the specimen may be a living organism, such as an animal or mammal. A target compound is bound to selected portions of deep tissue in the specimen. An illuminator 120 (e.g., a metal halide lamp or other lamp, a laser, an light emitting diode array, or any other source of electromagnetic radiation) directs excitation light 122 to the specimen to excite emission (e.g., fluorescence) from the target compound in the deep tissue. Typically, the excitation light will also cause the autofluoresence from the other components in the specimen. Therefore, the electromagnetic radiation 130 emitted from the specimen includes emission from the target compound as well as autofluorescence. Emitted radiation 130 is collected by imaging system 140 and imaged onto a camera 150.

Because system 100 is designed for imaging deep tissue in relatively large specimens (e.g., living organisms), the imaging system typical provides a demagnification of one or more, or even 2 or more. That is, the image on the camera is the same size or smaller than the object field of view for the imaging system. Also, the object field of view for the imaging system is typically greater than about 2 cm (or greater than about 3 cm) along a diagonal dimension.

Furthermore, although FIG. 10 shows emitted radiation 130 as being collected from an opposite side of the specimen relative to excitation light 122, in other embodiments, the emitted radiation can be collected from the same side as, or at an angle to, that illuminated by the excitation light. Moreover, illumination may be provided from multiple sides of the specimen.

Positioned between the specimen and camera 150 is a tunable optical filter 160 (e.g., a liquid crystal, tunable optical filter, an interferometric optical filter, or a motorized filter wheel). Optical filter 160 spectrally filters emitted radiation 130 according to each of a plurality of spectral weighting functions (for example, four or more spectral weighting functions). The spectral weighting functions may correspond to specific wavelength bands, or may be more complicated functions such as a sinusoid distribution of pass bands. Camera 150 records images of the spectral filtered emitted radiation 170 for each of the different spectral weighting functions, and sends the image data to a computer 180 for analysis. As described in greater detail below, the computer processes the image data based on the different spectral weighting functions, and one or more emission spectra corresponding to pure target compound, pure autofluorescence of one or more other components of the specimen, or both, to construct a deep tissue image that suppresses the autofluorescence signal to reveal the target compound.

In what follows, we describe the context for the spectral imaging of the deep tissue, a specific example of deep tissue imaging, and spectral unmixing techniques for constructing the deep tissue image.

It is a hallmark of imaging structures in deep-tissue samples via target compounds that the optical signals are relatively weak. Accordingly, many practitioners place prime importance on the properties of the detector, and on the efficiency of all elements in the optical path, such as the lenses and the blocking filter used to block the excitation light from reaching the detector. Yet while the present art of CCD detectors and the like is suitable for detecting low light level signals, it does not adequately address the problem of discriminating between light emitted by the target compound, and light from other sources such as autofluorescence. Thus one's detection level in practice may be set by the level of confounding light arising from sites elsewhere within the specimen, rather than considerations such as readout noise in one's detector, or the light gathering power of the objective.

Put more precisely, one's detection limit can be seen as the greater of one's detector noise or the confounding signal flux which is presented to the detector; expressed in either case as the equivalent concentration of target compound in the specimen to produce light of that signal level at the detector.

Unless the light emitted by the target compound dominates over all other sources in the specimen, one is often limited by the confounding signal rather than by one's detection apparatus. Some level of autofluorescence is inherent in biological samples when they are illuminated with light of visible range, especially when the light is green (550 nm) or shorter. So despite the use of optimized target compounds, autofluorescence arising at or near the specimen surface can often set the detection limit.

Further, emission from target compounds within deep tissue can be attenuated by scattering or absorption as it travels from the site of emission to the surface of the specimen. The signal level reaching the imaging system is thus reduced, while light that is generated at the surface layer of the specimen is not similarly attenuated. The details of this effect depend on the geometry of the sample specimen relative to the collection optics, as well as the optical properties of the sample.

Likewise, the illumination light may be attenuated or scattered as it travels from the source of illumination through the surface layers of the specimen on its way to the structure being imaged. The excitation signal reaching the target site is reduced, while the signal developed at the surface of the specimen is not similarly attenuated. The details of this depend on the geometry of the illumination and collection optics, as well as on the optical properties of the sample specimen.

These considerations can exacerbate the effect of autofluorescence by increasing the relative contribution of autofluorescence emission to the detected signal, compared with emission from the target compound.

Figure 1:
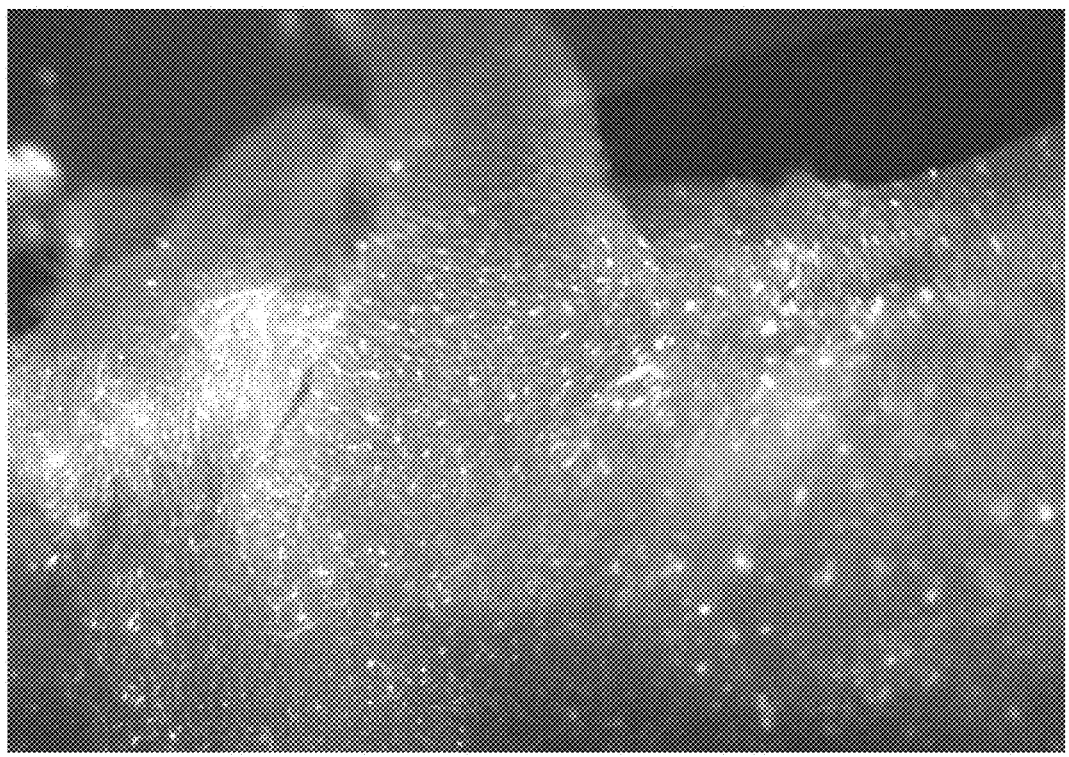
FIG. 1 is an image of a mouse which has been injected with a fluorescent probe, imaged at a single spectral band of $\lambda=530$ nm.

The magnitude of the problem is illustrated by FIG. 1, which is an image of the fluorescent emission from a mouse. The mouse was illuminated with light of approximately 480 nm, and the emission light was filtered by a 25 nm bandpass filter centered at 530 nm. There is a tumor in the lung of the mouse which expresses the green fluorescent protein (GFP). Yet the tumor is not easily distinguishable in the image due to an equal or greater signal from generalized autofluorescence, apparently developed in the dermal layers of the mouse. As a result, while the signal level at any point in the image is easily quantified, the presence of target compound, and thus the tumor, cannot be confirmed due to high levels of background autofluorescence which sets an equal or higher detection threshold than the target compound involved.

Autofluorescence is also variable from specimen to specimen and can be unpredictable. Thus if an absolute flux level is used to make assessments about the target compound, one can obtain false positive readings. Variability can arise from factors such as mold or disease on the skin of the specimen. These are typically not uniform across the specimen. So if one seeks to detect the presence of a target compound by comparing local signal levels in a given region against the mean level for the specimen, results are also not reliable.

Figure 2:
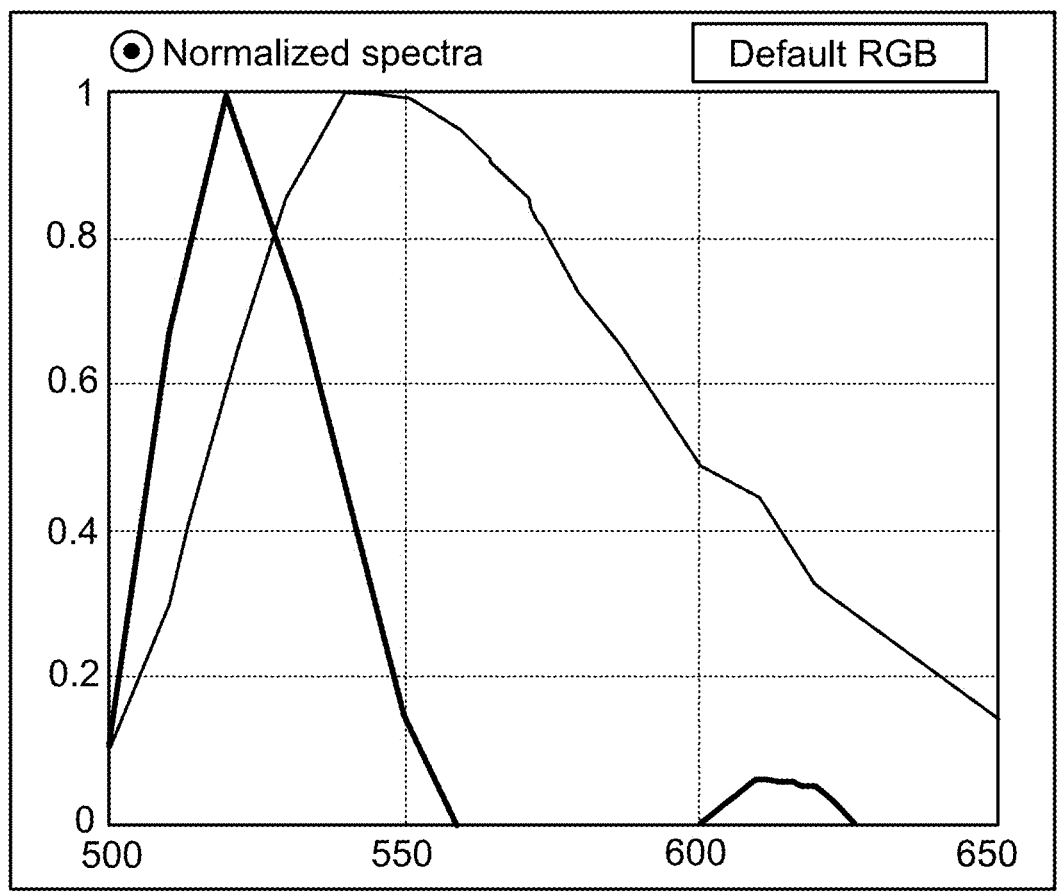
FIG. 2 is a graph of the emission spectrum of autofluorescence and that of the target compound for the sample of FIG. 1, with the light-colored line showing the spectrum for the autofluorescence and the dark-colored line showing the spectrum for the target compound.

It is possible in some cases to reduce autofluorescence by choice of the illumination wavelength. Generally the use of longer wavelengths for illumination is beneficial, as is known in the art, since they typically generate less autofluorescence. Also, it can be beneficial to choose a target compound whose emission light occurs at a different wavelength range from the autofluorescence of the specimen. Yet it is not possible to choose wavelengths that is free of crosstalk, as shown by FIG. 2. The emission spectra of the target compound, GFP (shown by the dark-colored line), and of the autofluorescence (shown by the light-colored line), are completely overlapping. At any wavelength where the target has substantial emission, the autofluorescence is also strong, so autofluorescence cannot be eliminated by use of a fixed optical filter or something similar. Nor does a color camera discriminate between two such similar green spectra.

Yet as FIG. 2 indicates, the spectra of GFP and autofluorescence emissions are nonetheless different. Thus, in accordance with the invention, a spectral imaging approach can distinguish the two and eliminate or greatly reduce the contribution of the latter signal.

In a first embodiment of the invention, this is achieved with conventional apparatus to illuminate the specimen and to block the illumination light from entering the detector. This can be done using an illuminator such as the LT-9500 MSYS from Lighttools Research (Encinitas, Calif.) together with a longpass optical filter that transmits substantially all light $\lambda > 510$ nm, placed in the path of the objective.

The spectral imaging detector consists of a QImaging 1300C digital cooled CCD camera (Roper Scientific, Trenton N.J.) with a 55 mm F/2.8 Nikkor macro lens (Nikon USA, Melville N.Y.), to which a VARISPEC tunable optical filter (CRI Inc, Woburn Mass.) is coupled with a mounting adaptor. The VARISPEC filter is a computer-controlled optical filter with 25 nm bandpass and tunable center wavelength. These are connected to an IBM Thinkpad computer which controls the image acquisition and performs the data analysis. Communication is via an IEEE-1394 interface to the camera, and an RS-232 interface to the VARISPEC filter.

The VARISPEC filter uses nematic liquid crystal variable retarder elements to construct a tunable Lyot filter. The variable retarders are placed in optical series with fixed waveplates of quartz or other material, to produce a retardance that is well-known and electrically adjustable. Linear polarizers between successive stages of the filter act to block unwanted orders so only a single peak is transmitted, and out-of-band leakage can be reduced to 0.01% if desired. By choice of the retarder thicknesses, one may obtain bandwidths ranging from 0.1 nm to 50 nm or more. Tuning action is rapid (<50 ms) and there is no image shift from tuning, which is valuable for imaging applications.

The mouse was imaged by taking a sequence of images while the center wavelength of the VARISPEC filter was tuned from 500 nm to 650 nm. The result is an image cube, with a full two-dimensional image of the sample, and a full spectrum at every point in the image. The exact spectrum recorded at a given point depends on the amount of GFP and autofluorescence, and on the two spectra, as:

$$S(x,y,\lambda)=a(x,y)*F(\lambda)+b(x,y)*G(\lambda) \quad [1],$$

where (x,y) indices are used to denote a given pixel location in the image, the asterisk "*" denotes multiplication, $\lambda$ is used to denote a given wavelength of emission or detection, and $S(x,y,\lambda)$ denotes the net signal for a given location and wavelength, $F(\lambda)$ denotes the emission spectrum of autofluorescence, $G(\lambda)$ denotes the emission spectrum of GFP, $a(x,y)$ indicates the abundance of autofluorescence at a given (x,y) location, and $b(x,y)$ indicates the abundance of GFP at a given (x,y) location.

Equation [1] states that the net signal from a given location is the sum of two contributions, weighted by the relative amount of autofluorescence and GFP present. It is easier to see if one writes the above equation for a single pixel:

$$S(\lambda)=aF(\lambda)+bG(\lambda) \quad [2].$$

F and G may be termed the spectral eigenstates for the system, which are combined in various amounts according to the amount of autofluorescence and GFP emission, to produce an observed spectrum S.

Now if the emission spectra of the autofluorescence and of the GFP are known (or can be deduced, as described below), one may invert equation [2] by linear algebra to solve for a and b, provided that the spectrum S has at least two elements in it; i.e. that one has data for at least two emission wavelengths $\lambda$. Then we can write $$A=E^{-1}S \quad [3],$$

where

A is a column vector with components a and b, and

E is the matrix whose columns are the spectral eigenstates, namely [F G].

Using equation [3] one can take the observed spectrum and calculate the abundance of the autofluorescence and of the GFP sources. This process may be repeated for each pixel in the image, to produce an image of GFP that is free of contributions from autofluorescence. As a result, the detection level is greatly enhanced.

Note that the matrix E need only be inverted once for a given set of autofluorescence and target compound spectra, so the calculation of abundances is not burdensome and can be readily done in nearly real-time by a personal computer.

Figure 3:
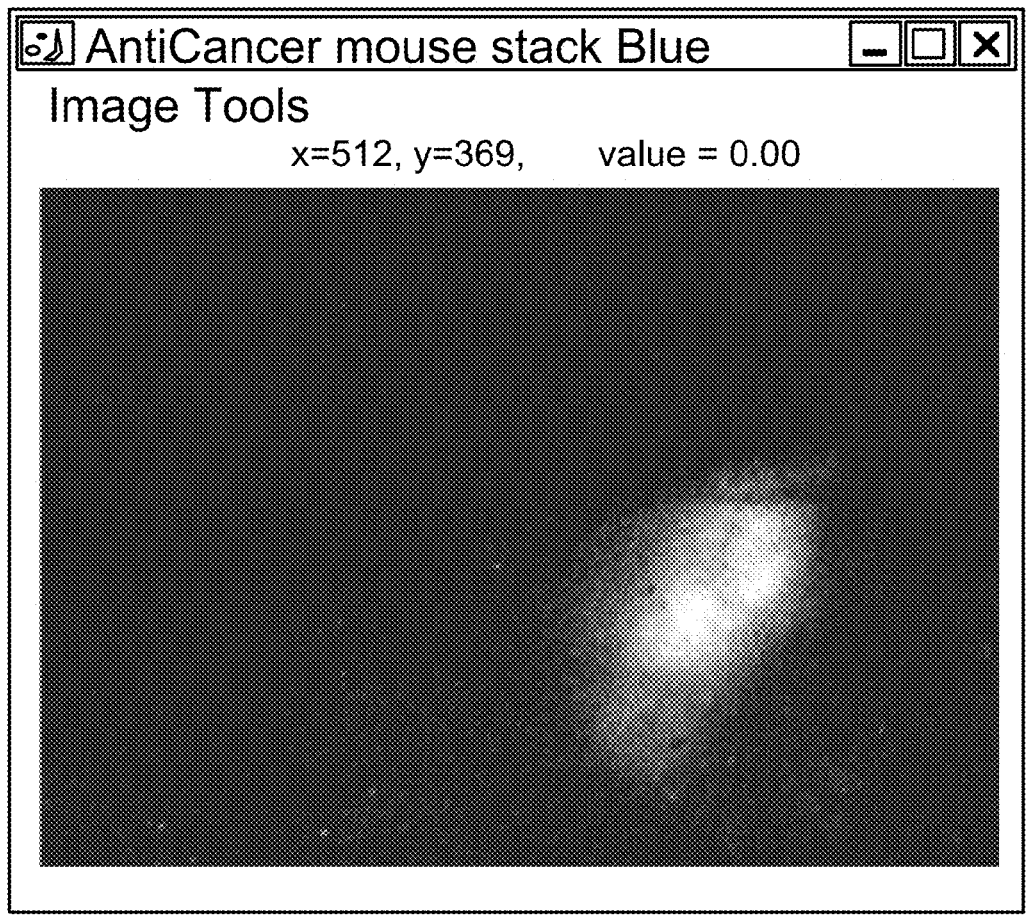
FIG. 3 is an image of the target compound emissions from the mouse of FIG. 1, with the autofluorescence signal removed using spectral techniques in accordance with the present invention.
Figure 4:
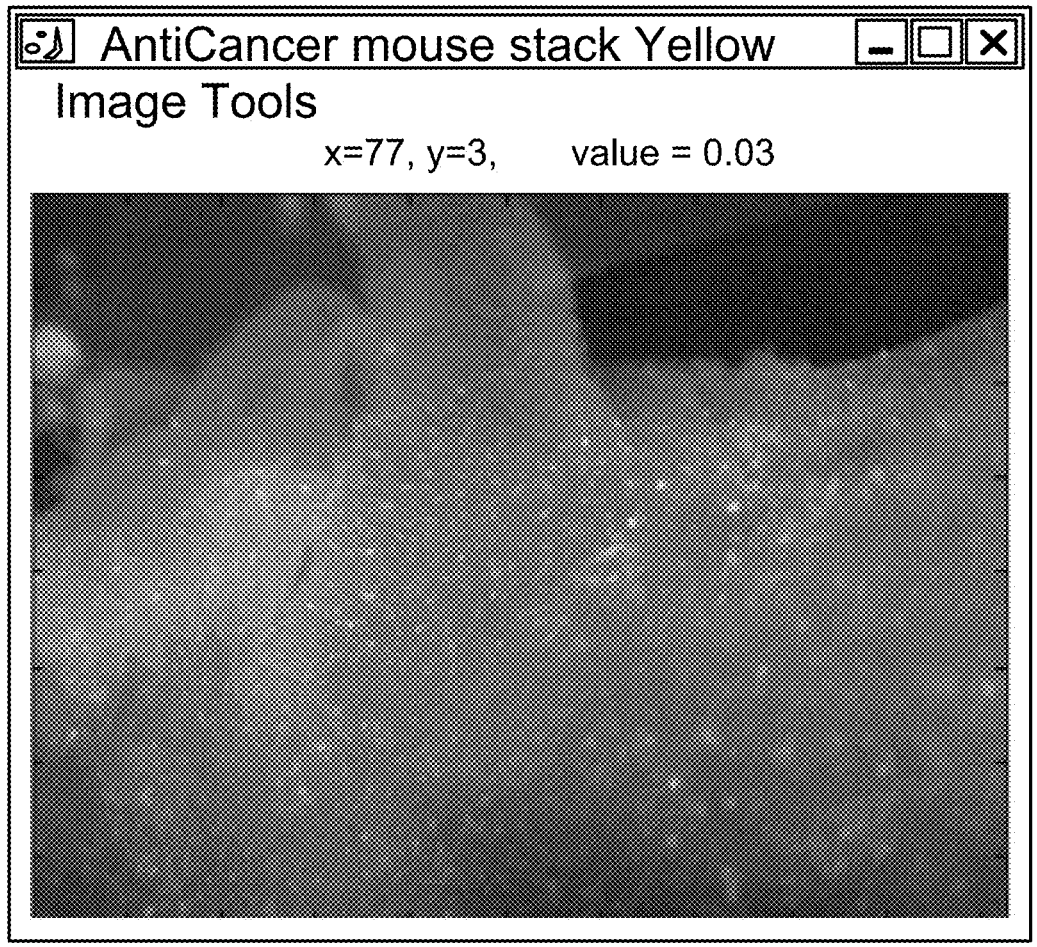
FIG. 4 is an image of the autofluorescence emissions from the mouse of FIG. 1, with the target compound emissions separated using spectral techniques in accordance with the present invention.

The results of this process are shown in FIGS. 3 and 4, which present the abundance images for GFP and autofluorescence, respectively. As FIG. 3 shows, it is easy to detect the GFP once it is separated from the autofluorescence. The degree of improvement in the GFP image is striking. Also, one can see that the autofluorescence image is smooth and unaffected in the region where GFP is present, which is consistent with the fact that the presence of GFP in a deep tissue structure should not alter the amount of autofluorescence emission from the overlying dermal regions.

Figure 5:
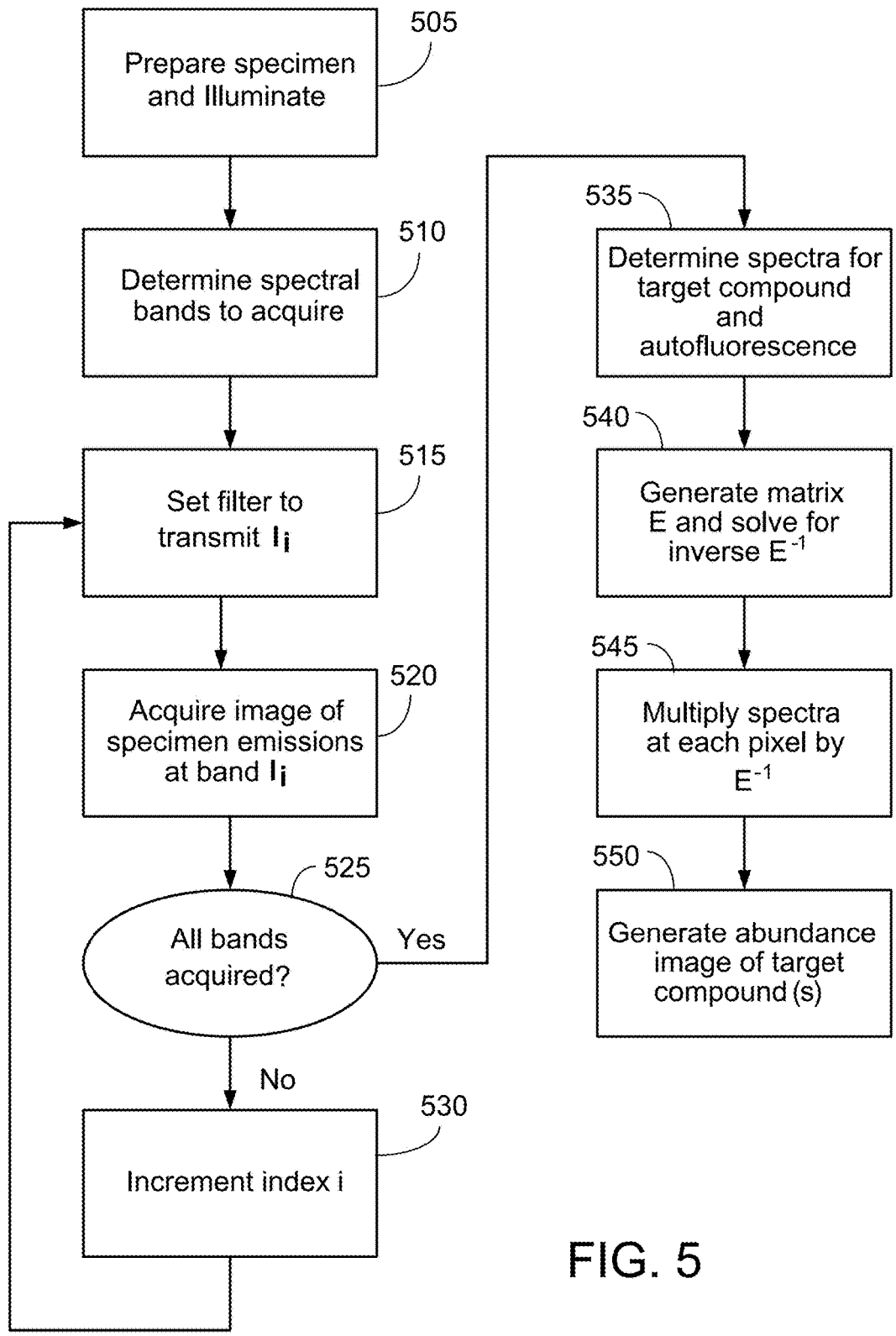
FIG. 5 is a flow-chart of one embodiment of the present invention, based on acquisition of a spectral cube and subsequent analysis by linear unmixing.
Figure 6:
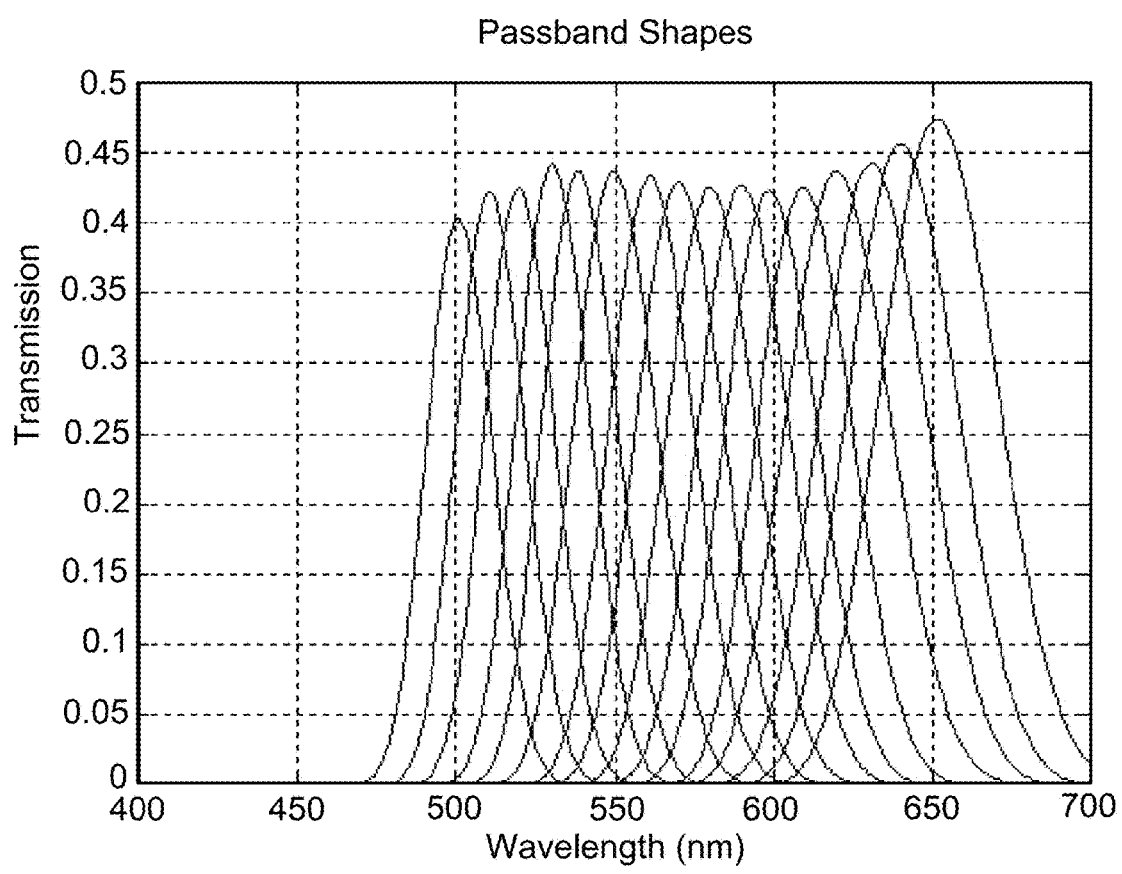
FIG. 6 is graph of the spectral properties of each spectral band in the embodiment of FIG. 5.

Overall, the measurement and analysis process is shown as a block diagram in FIG. 5. The specimen is prepared and illuminated (step 505) and the spectral bands to be acquired determined (step 510). Then the spectral filter is set to transmit the spectral weighting function $I_t$, for example, a particular wavelength band (step 515), and an image corresponding to that spectral weighting function is acquired (step 520). The spectral filter is then set to the next spectral weighting function and the corresponding image acquired until all bands have been acquired (steps 525 and 530). The spectra for the target compound and the autofluorescence is then provided or otherwise determined (step 535). Based on the spectra, the matrix E is generated and its inverse determined (step 540). For each image pixel, the spectra defined by the series of acquired images is then multiplied by the inverse matrix of E (step 545) to generate an abundance image of the target compound(s), i.e., the deep tissue image (step 550).

In this example, the invention permitted observation of structures in tissue lying ~2 mm within a living organism, where the overlying dermis is at least 300 microns thick and has significant autofluorescence. The invention has also been used to image structures at differing depths in other specimens, including non-mammalian specimens such as zebrafish. In the latter, the specimen is physically thinner, but once again there is the problem of autofluorescence arising from other layers in the specimen, which confounds the detection of target compounds in the interior of the specimen. While there are optical techniques for depth sectioning, such as confocal microscopy, the present invention provides a simple and practical alternative.

Nothing about this invention prevents one from viewing multiple target compounds per specimen. If we denote the number of spectral settings as n, matrix E becomes an n×m matrix instead of an n×2 matrix used in the above example. So, one can use the invention to remove autofluorescence from a sample which contains two target compounds; or to remove two types of autofluorescence from a sample with one or more target compounds. In any case, the result is the isolation of the target compound(s) from the autofluorescence, and the ability to quantify one or all of these components.

The limit to the number of compounds that can be isolated, and to the signal to noise generally, is given by the shot noise levels and the degree of spectral distinction between the emission spectra of the species being distinguished (including autofluorescence). One can describe the degree of correlation between two spectra by an angle $\theta$, defined by $$\theta = \arccos\left[(S_1 \cdot S_2)/(|S_1||S_2|)\right] \quad [4].$$

Sets of spectra for which $\theta$ is small for two members are not as easily separated into their components. Physically, the reason for this is easily understood: if two spectra are only marginally different, it is harder to determine which species was present, and noise can easily change one's estimate of relative abundances. Criteria such as $\theta$ can be used to help decide what spectral bands are appropriate for a measurement, and one may try and select bands that yield a large $\theta$ whenever possible. Or, one may make an empirical study of what bands yield the best separation, by trial and error. It can be helpful to include more bands than would appear necessary from mathematical analysis alone, in order to reduce sensitivity to slight spectral shifts from the expected shapes, as may occur due to variation between specimens and the like.

It is worth considering the optical efficiency of the measurement apparatus in the above embodiment, to understand where the inventive improvement comes from. First, the lens used was an F/2.8 type instead of an F/1.2 or F/1.8 which is more typical for this work, and this choice results in 2.4-5.4× less light collection. Next, the VARISPEC filter has a transmission of approximately 25 percent, and collects over a 25 nm range, in contrast to a typical interference filter which has a transmission of 80 percent and collects over a 40 nm range. This further reduces the sensitivity by a factor of 5.1× compared to equipment that might be used for this work, for an overall reduction in light flux of 12.3×-27.8× compared to the best practice alternatives of the art.

The CCD camera is cooled 25° below ambient to approximately 0° C., which is typical for an ordinary CCD sensor, unlike the sensors used in imaging stations such as the ChemiPro system from Roper Scientific (Trenton, N.J.), which is cooled with liquid nitrogen to attain temperatures 100° below ambient or lower.

As this suggests, the effectiveness of this technique does not arise from extreme efficiency in the gathering or collection of light; rather it comes from using spectral selectivity to identify and remove the effects of background fluorescence.

Turning now to the question of how the spectra F and G are determined, any method may be used which yields an adequate estimate of the spectra involved. For some target compounds, there is a known spectrum for the material from published references. Alternatively, with a spectral imaging station as is used in the invention, one may obtain the spectrum directly by placing a sample containing a sufficient concentration of the target compound in front of the imager and taking its spectrum. Conversely, it is often possible to image a region of the specimen where one has a priori knowledge that there is no target compound in that region, and in this way one can obtain an estimate of that component.

Various data analysis techniques can be used in this process, such as principal component analysis (PCA), which identifies the most orthogonal spectral eigenvectors from an image cube, and yields score images showing the weighting of each eigenvector throughout the image. If PCA analysis is performed on an image that contains contributions from the target compound(s) and from the background autofluorescence, the vectors from PCA can be used to develop estimates of the spectra involved.

This may be done in combination with other mathematical processing, and there are other known techniques for identifying low-dimensionality spectral vectors, such as projection pursuit, a technique described in L. Jimenez and D. Landgrebe, "Hyperspectral Data Analysis and Feature Reduction Via Projection Pursuit", *IEEE Transactions on Geoscience and Remote Sensing*. Vol. 37, No. 6, pp. 2653-2667, November 1999.

Figure 7:
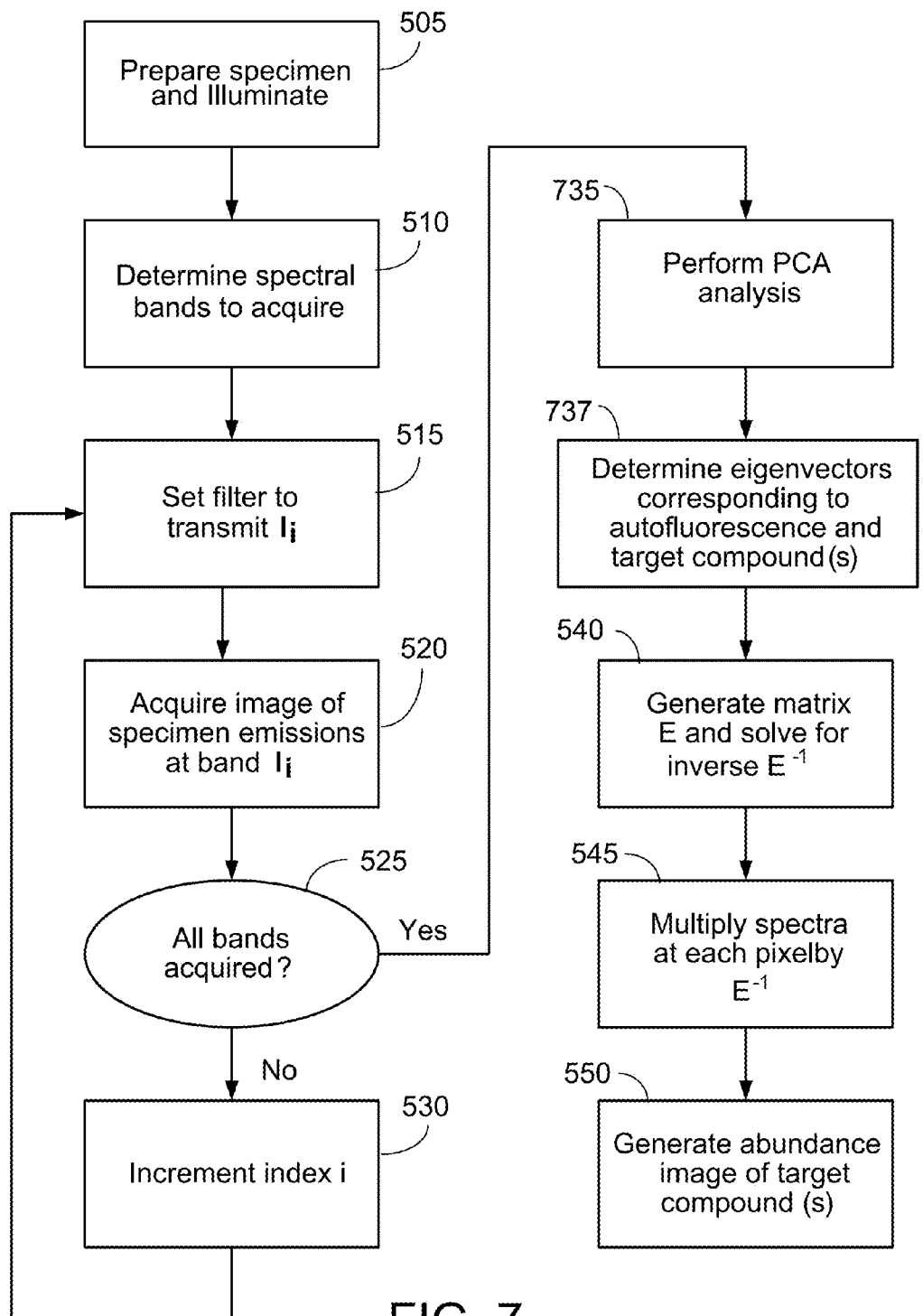
FIG. 7 is a flow-chart of another embodiment which incorporates PCA to estimate the spectra of the autofluorescence and the target compound(s).

An embodiment that incorporates PCA is shown in FIG. 7 in block-diagram form. The block diagram is similar to that of FIG. 5, except that step 535 is replaced with performing a PCA analysis (step 735) and determining eigenvectors corresponding to the autofluorescence and target compound(s) (step 737) for use in the matrix E in step 540.

Whatever method is used in the determination, the goal is to derive spectra corresponding to the species sought, whether the determination is made by a direct measurement of relatively pure samples of the target compound and the autofluorescence, or a mathematical analysis of spectra that may contain mixtures of both components, so long as adequate spectral estimates are obtained.

While the embodiments discussed above use spectral estimates for both the autofluorescence emissions and target compound emissions, this is not essential. In some cases, one may seek to reduce the autofluorescence without having a priori knowledge of the target compound spectrum. This can be done by looking at the signal in a given pixel, and subtracting from it the maximum amount of autofluorescence while leaving the remaining signal that is positive definite in all spectral channels. That is, one defines a so-called remainder spectrum $R_a(\lambda)$ for each pixel:

$$R_a(\lambda)=S(\lambda)-aF(\lambda) \quad [5a],$$

and then selects the largest value of parameter a consistent with $R_a(\lambda)$ having a non-negative value in every spectral channel. The resulting spectrum $R_a(\lambda)$ is then used as the sample spectrum, expunged of autofluorescence. One may also make the determination of a based not on strict non-negative criterion listed above, but on some related criteria that incorporates a small negative distribution, to account for considerations such as shot noise or detector noise.

Alternatively, one may seek to determine the distribution of the target compound by a similar method when its emission spectrum is known, but the autofluorescence spectrum is not, by seeking to subtract off from $S(\lambda)$ the maximum amount of target emission $G(\lambda)$ consistent with a positive remainder, and then reporting the amount that was subtracted at each pixel as the image of the target compound. In this case, the remainder spectrum $R_b(\lambda)$ for each pixel is given by:

$$R_b(\lambda)=S(\lambda)-bG(\lambda) \quad [5b],$$

where one selects the largest value of parameter b consistent with $R_b(\lambda)$ having a non-negative value in every spectral channel.

Furthermore, the technique described above in connection with Equations 5a and 5b can be expanded to cases where the spectra for one or more additional components of the sample are known, and one wants to remove their contribution to the signal. In such cases the remainder spectrum is rewritten to subtract a contribution of each such component from the observed signal based on the additional spectra and consistent with a positive remainder in each spectral channel.

Another preferred embodiment uses the same apparatus to illuminate and view the specimen, except that the specimen is a zebrafish in an aqueous sample stage.

Yet another alternative uses the same apparatus to view a mouse that has been transfected to express either the yellow fluorescent protein (YFP) or the red fluorescent protein (RFP), or both, and produces images of the target compound (s) after removal of the autofluorescence signal. There are also mutant strains developed which may also be used. Any of these may be combined with the GFP when that produces useful results.

Further alternative embodiments view mice containing target compounds based on quantum dots, and incorporate an illuminator and filter set optimized for the quantum dot species involved.

An embodiment operating in the infrared range 600-1100 nm may also be constructed using a near-infrared VARISPEC filter such as the model VIS-NIR2-10-20HC.

In an alternative embodiment, the VariSpec filter is replaced with a motorized filter wheel containing a plurality of bandpass filters. Yet another embodiment uses a split-image system from Optical Insights (Tucson, Ariz.) to view the specimen in four spectral bands at once, albeit with lower spatial resolution. The bands are chosen to give a spectrum that distinguishes between the target compound and background autofluorescence, i.e. to have cos θ that is significantly different from 1, preferably 0.8 or less.

Figure 8:
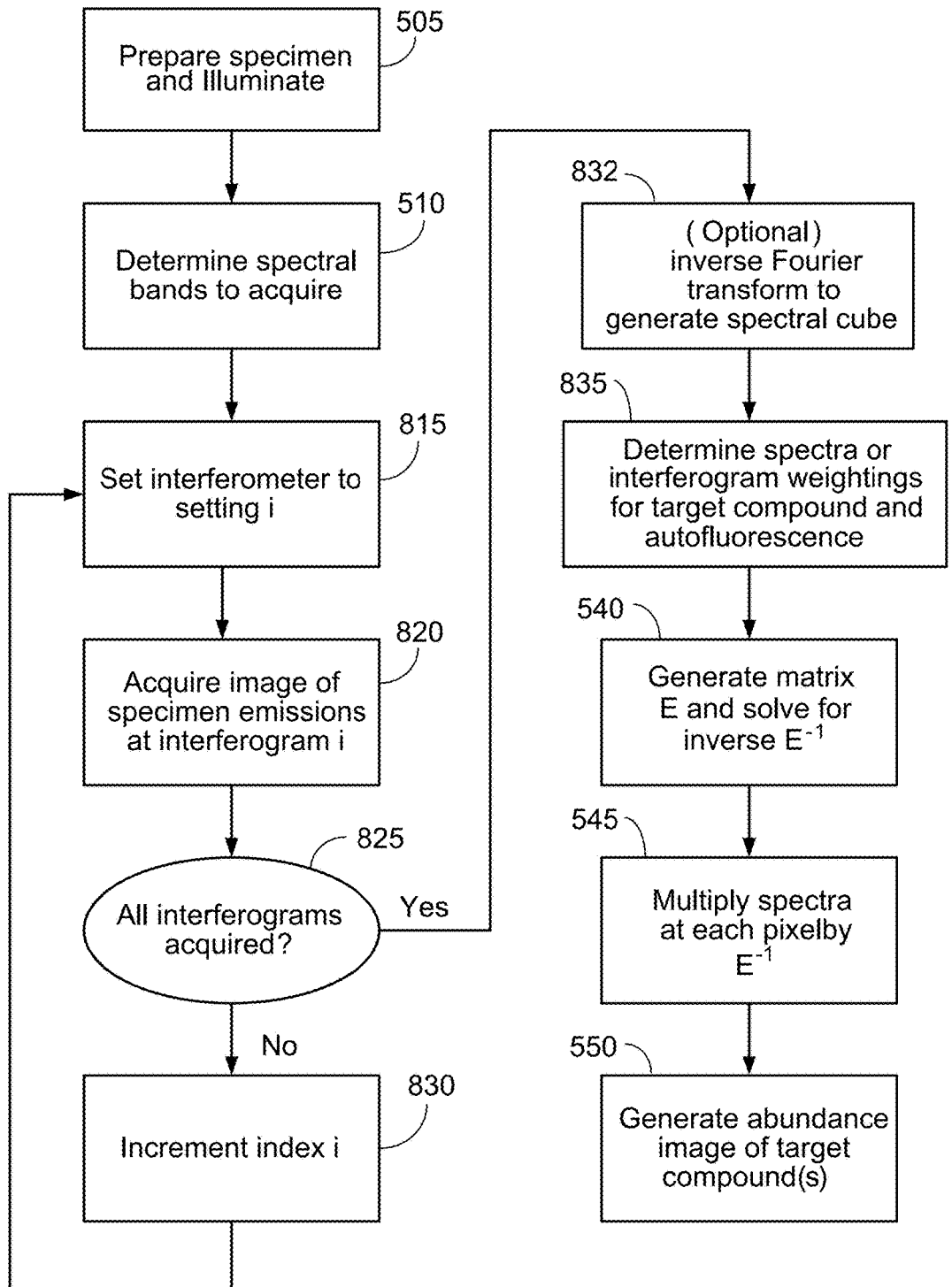
FIG. 8 is a flow-chart of yet another embodiment in which the spectral filtering is performed interferometrically.
Figure 9:
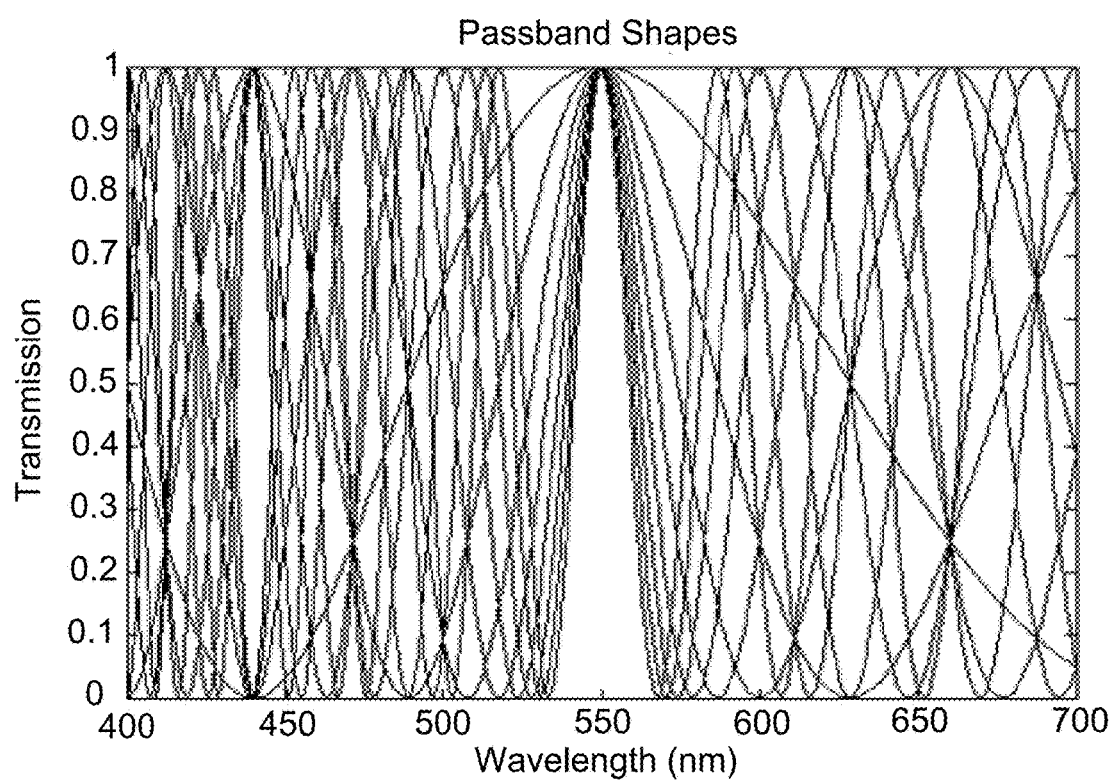
FIG. 9 is a graph of the spectral properties of the spectral weightings used in the embodiment of FIG. 8.

It is not necessary that the images used for the spectral analysis be acquired with bandpass filters, only that the spectral weightings of the various images be different. For example, one could use an interferometer to acquire the spectral information, as shown in FIG. 8 in block-diagram form. The spectral response of the interferometer is shown in FIG. 9 for some selected values of path difference Z. Images thus obtained can be used for practicing the invention, either directly or after transforming from interferograms to spectra. The suitability of using the interferograms can be checked by looking at how well they distinguish between the species involved, which can be determined by measures such as cos θ or by experimental study.

The block diagram of FIG. 8 is similar to that of FIG. 5 except that: steps 515, 520, 525, and 530 are replaced with corresponding steps 815, 820, 825, and 830, which use a interferogram as the spectral weighting function rather than particular spectral bands; there is an optional step 832, which describe Fourier transforming the spectrally filtered images to generate a spectral cube; and step 535 is replaced with step 835 determines spectra or interferogram weightings for the target compound and the autofluorescence consistent with the form of the acquired data (and optional Fourier transform) for use in generating the matrix E.

The interferometer can be a mechanical type such as a Sagnac design, or it can be a birefringent interferometer as described in U.S. Pat. No. 6,421,131, "Birefringent interferometer". The latter uses fixed retarder elements such as quartz plates, together with switching apparatus, to make the retarders add or cancel one another, so that using these elements, along with variable retarder elements, one can produce any desired retardance within a wide range. When polarized light encounters this assembly, its polarization state is changed in a manner that depends on the wavelength of light, and this can be detected at an exit analyzer polarizer. The spectral response at any particular setting of the interferometer is a sinusoid in $1/\lambda$, after allowing for dispersion. By taking a sequence of readings at known retardance values, and performing a fourier transform, the spectrum of the light can be determined. Such apparatus can be used in imaging systems to obtain a spectrum at every point in an image, or simply to obtain a set of images with various sinusoidal spectral response functions in the members of the set.

Indeed, any spectral imaging apparatus can be used provided that it yields adequate spectral information to distinguish emission by the target compound from background autofluorescence.

The spectral analysis and construction of the deep tissue image can be implemented in hardware or software, or a combination of both. The electronic processing can be implemented in computer programs using standard programming techniques following the methods described herein. Program code is applied to input data to perform the spectral unmixing functions described herein and generate output information such as the deep tissue image. The output information is applied to one or more output devices such as a display monitor.

Each program is preferably implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., CD-ROM or magnetic diskette) readable by a general or special purpose programmable computer, for configuring and operating the computer when the storage media or device is read by the computer to perform the procedures described herein. The computer program can also reside in cache or main memory during program execution. For example, computer 180 in FIG. 10 may includes a processor, an input/output control card, a user interface, such as a keyboard and monitor, and a memory. A program stored on a computer-readable medium is stored in the computer memory, and when executed, the program causes the processor to carry out the steps of analyzing the spectrally filtered images.

While certain embodiments have been described, alternatives may be used that achieve the same end without deviating from the spirit of the invention, according to the requirements of the task at hand and normal design considerations. It is explicitly intended that this invention can be combined with the arts of instrument design, multispectral data analysis and image analysis, and optical system design, as appropriate for a given use.

Additional aspects, features, and advantages are within the scope of the following claims.

What is claimed is:

1. A method comprising:
   illuminating a sample to cause the sample to emit radiation, wherein the sample comprises deep tissue supporting a target compound and one or more additional components, and wherein the emitted radiation comprises emission from the target compound and emission from the one or more additional components;
   spectrally filtering the emitted radiation with each of a plurality of different spectral weighting functions;
   storing an image of the spectrally filtered radiation for each of the spectral weighting functions; and
   processing the stored images to construct a deep tissue image of the sample comprising a signal contribution from the target compound and a signal contribution from each of the one or more additional components so that in the deep tissue image, the signal contributions from each of the one or more additional components are reduced relative to the signal contribution from the target compound,
   wherein processing the stored images comprises constructing the deep tissue image based on the stored images and an emission spectrum for the target compound.

2. The method of claim 1, wherein the sample comprising the deep tissue is a living organism.

3. The method of claim 2, wherein the living organism is an animal.

4. The method of claim 3, wherein the living organism is a mammal.

5. The method of claim 3, wherein the animal comprises a mouse, a zebrafish, or a human.

6. The method of claim 2, wherein the deep tissue is an internal organ of the living organism.

7. The method of claim 1, wherein the sample is an organism, and wherein the deep tissue is subdermal tissue that lies within about 2 mm or more of the organism.

8. The method of claim 1, wherein the emission from other components of the sample comprises autofluorescence from one or more layers of tissue in the sample different from a layer of tissue comprising the deep tissue.

9. The method of claim 1, wherein the target compound is a fluorescent probe bound to at least a portion of the deep tissue.

10. The method of claim 1, wherein the target compound is a quantum dot bound to at least a portion of the deep tissue.

11. The method of claim 1, wherein the target compound is comprises at least one of a green fluorescent protein (GFP), a yellow fluorescent protein (YFP), and a red fluorescent protein (RFP) bound to at least a portion of the deep tissue.

12. The method of claim 1, wherein the emission from the target compound is fluorescence.

13. The method of claim 1, wherein at least some of the spectral weighting functions correspond to particular wavelength bands.

14. The method of claim 13, wherein all of the spectral weighting functions correspond to particular wavelength bands.

15. The method of claim 1, wherein at least some of the spectral weighting functions correspond to sinusoidal weightings of multiple wavelength bands.

16. The method of claim 1, wherein the spectral filtering comprises at least one of: using a liquid-crystal, tunable optical filter, using an interferometric optical filter, and using a filter wheel comprising a plurality of band pass filters.

17. The method of claim 1, wherein each stored image comprises an intensity value for each of multiple pixels.

18. The method of claim 1, wherein processing the stored images comprises constructing the deep tissue image based on a weighted superposition of signals in the stored images.

19. The method of claim 1, wherein processing the stored images comprises constructing the deep tissue image based on at least one emission spectrum corresponding to the one or more additional components in the sample.

20. The method of claim 19, wherein constructing the deep tissue image comprises calculating a remainder spectrum for each pixel in the set of stored images.

21. The method of claim 1, wherein the deep tissue supports multiple target compounds and processing the stored images comprises constructing a deep tissue image for each of the target compounds.

22. The method of claim 21, wherein processing the stored images comprises constructing the deep tissue images based on the stored images and emission spectra for each of the target compounds.

23. The method of claim 22, wherein processing the stored images comprises constructing the deep tissue images based on the stored images, the emission spectra for each of the target compounds, and at least one emission spectrum for the one or more additional components in the sample.

24. The method of claim 1, wherein the plurality of the different spectral weighting functions comprises at least four spectral weighting functions.

25. A method comprising:
   providing a plurality of images of spectrally filtered radiation emitted from a sample in response to an illumination,
   wherein the sample comprises deep tissue supporting a target compound and one or more additional components,
   wherein the emitted radiation comprises emission from the target compound and emission from the one or more additional components, and
   wherein each image corresponds to a different spectral weighting function applied to the emitted radiation; and
   processing the images of the spectrally filtered radiation to construct a deep tissue image of the sample in which a signal contribution from each of the one or more additional components is reduced relative to a signal contribution from the target compound,
   wherein the processing the images of the spectrally filtered radiation comprises constructing the deep tissue image based on the stored images and an emission spectrum for the target compound.

26. An apparatus comprising:

a sample holder configured to hold a sample comprising deep tissue, wherein the deep tissue supports a target compound and one or more additional components;

an illumination source configured to illuminate the sample to cause the sample to emit radiation, wherein the emitted radiation comprises emission from the target compound and emission from the one or more additional components;

an imaging system configured to image the emitted radiation to a detector;

a tunable spectral filter configured to spectrally filter the emitted radiation with each of a plurality of different spectral weighting functions;

a detector configured to store an image of the spectrally filtered radiation for each of the spectral weighting functions; and an electronic processor configured to process the stored images to construct a deep tissue image of the sample based on the stored images and an emission spectrum for the target compound, in which a signal contribution from each of the additional components is reduced relative to a signal contribution from the target compound.

27. The apparatus of claim 26, wherein the sample holder is configured to hold an animal.

28. The apparatus of claim 26, wherein the imaging system is configured to image a field of view having a diagonal dimension greater than about 2 cm onto the detector.

* * * * *

UNITED STATES PATENT AND TRADEMARK OFFICE
CERTIFICATE OF CORRECTION

PATENT NO. : 9,588,099 B2  
APPLICATION NO. : 13/760193  
DATED : March 7, 2017  
INVENTOR(S) : Richard Levenson and Paul J. Cronin Page 1 of 1

It is certified that error appears in the above-identified patent and that said Letters Patent is hereby corrected as shown below:

On the Title Page

Column 1 (Assignee), Line 2, delete "Intrumentation," and insert -- Instrumentation --

In the Claims

Column 14
Line 2, in Claim 11, before "comprises" delete "is"

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*